United States Patent
Kwan et al.

(10) Patent No.: US 9,861,263 B2
(45) Date of Patent: Jan. 9, 2018

(54) POLYMERIC MATERIAL FOR USE IN AND WITH STERILIZABLE MEDICAL DEVICES

(71) Applicant: KARL STORZ Imaging, Inc., Goleta, CA (US)

(72) Inventors: Kin Ming Kwan, Goleta, CA (US); Dejan Korkut, Santa Barbara, CA (US); Thomas J. Anhalt, Goleta, CA (US); Paul McCarty, Carpinteria, CA (US); Diegas E. Zavala, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 15/334,249

(22) Filed: Oct. 25, 2016

(65) Prior Publication Data

US 2017/0035270 A1    Feb. 9, 2017

Related U.S. Application Data

(62) Division of application No. 14/614,095, filed on Feb. 4, 2015, now Pat. No. 9,526,403.

(51) Int. Cl.
*A61B 1/00* (2006.01)
*B29D 15/00* (2006.01)
(Continued)

(52) U.S. Cl.
CPC ........ *A61B 1/0011* (2013.01); *A61B 1/00066* (2013.01); *A61B 1/00105* (2013.01); *A61B 1/00142* (2013.01); *A61B 1/045* (2013.01); *A61B 90/08* (2016.02); *A61B 90/361* (2016.02); *A61L 31/022* (2013.01); *A61L 31/028* (2013.01);
(Continued)

(58) Field of Classification Search
CPC .............. A61B 1/0011; A61B 1/00112; A61B 1/00066; A61B 1/00105; A61B 1/00142; A61B 1/045; A61L 31/06; B22F 7/04; B29D 15/00; G05G 1/00; G05G 5/04; Y10T 74/2084; C08K 3/22; C08K 3/24; C08K 5/0041; C08K 5/18
See application file for complete search history.

(56) References Cited

U.S. PATENT DOCUMENTS 4,694,881 A    9/1987    Busk
4,694,882 A    9/1987    Busk
(Continued)

OTHER PUBLICATIONS

Kapoor, et al.; "Comparison of Sequential Valve Gate Molding to Multi-Cavity Melt Control Injection Molding"; Created Dec. 12, 2003, pp. 1-23.
(Continued)

*Primary Examiner* — Thomas C Diaz
(74) *Attorney, Agent, or Firm* — Michael Joseph Loi

(57) ABSTRACT

The invention provides an endoscopic video camera having a polymeric knob assembly, wherein the polymeric material used for manufacturing the knob assembly includes polyphenylsulfone resin, titanium dioxide, tin oxide, and colored metallic additives, is capable of withstanding sterilization, and has a metallic cosmetic appearance. The invention also provides methods of manufacturing the knob assembly by plastic injection molding processes, wherein undesirable molding characteristics are concentrated on portions of the knob assembly that are removed by secondary machining or post machining.

20 Claims, 14 Drawing Sheets

(51) Int. Cl.
| | |
|---|---|
| *G05G 1/10* | (2006.01) |
| *B22F 7/04* | (2006.01) |
| *G05G 5/04* | (2006.01) |
| *C08K 3/34* | (2006.01) |
| *C08K 3/22* | (2006.01) |
| *A61L 31/06* | (2006.01) |
| *A61B 1/045* | (2006.01) |
| *C08K 5/00* | (2006.01) |
| *C08K 5/18* | (2006.01) |
| *A61B 90/00* | (2016.01) |
| *A61L 31/02* | (2006.01) |
| *G02B 23/24* | (2006.01) |
| *B29K 81/00* | (2006.01) |
| *B29K 105/16* | (2006.01) |
| *B29K 505/08* | (2006.01) |
| *B29K 505/06* | (2006.01) |
| *B29K 509/10* | (2006.01) |
| *B29K 509/08* | (2006.01) |

(52) U.S. Cl.
CPC ............... *A61L 31/06* (2013.01); *B22F 7/04* (2013.01); *B29D 15/00* (2013.01); *C08K 3/22* (2013.01); *C08K 3/34* (2013.01); *C08K 3/346* (2013.01); *C08K 5/0041* (2013.01); *C08K 5/18* (2013.01); *G02B 23/2476* (2013.01); *G05G 1/10* (2013.01); *G05G 5/04* (2013.01); *A61B 2090/0813* (2016.02); *B22F 2007/042* (2013.01); *B29K 2081/06* (2013.01); *B29K 2105/16* (2013.01); *B29K 2505/06* (2013.01); *B29K 2505/08* (2013.01); *B29K 2509/08* (2013.01); *B29K 2509/10* (2013.01); *B29K 2995/0021* (2013.01); *C08K 2003/2231* (2013.01); *C08K 2003/2241* (2013.01); *C08K 2201/014* (2013.01)

(56) References Cited

U.S. PATENT DOCUMENTS

| | | |
|---|---|---|
| 5,040,589 A | 8/1991 | Bradley et al. |
| 5,064,463 A | 11/1991 | Ciomek |
| 5,577,546 A | 11/1996 | Kjar et al. |
| 5,836,867 A | 11/1998 | Speier |
| 5,848,350 A | 12/1998 | Bulger |
| 5,989,493 A | 11/1999 | La Salle et al. |
| 5,993,507 A | 11/1999 | Baum et al. |
| 6,298,901 B1 | 10/2001 | Sakamoto et al. |
| 6,350,328 B1 | 2/2002 | Hostetler |
| 6,470,956 B2 | 10/2002 | Sakamoto et al. |
| 6,478,842 B1 | 11/2002 | Gressel et al. |
| 6,514,269 B2 | 2/2003 | Yamamoto |
| 6,522,477 B2 | 2/2003 | Anhalt |
| 6,619,370 B2 | 9/2003 | Sakamoto et al. |
| 6,633,438 B2 | 10/2003 | Anhalt |
| 6,669,898 B2 | 12/2003 | Gressel et al. |
| 6,790,252 B2 | 9/2004 | Smith et al. |
| 6,838,046 B2 | 1/2005 | Lu et al. |
| 6,860,316 B2 | 3/2005 | Wu et al. |
| 6,890,368 B2 | 5/2005 | Braillard et al. |
| 7,311,674 B2 | 12/2007 | Gingrich et al. |
| 7,452,201 B2 | 11/2008 | Ciccone |
| 7,718,100 B2 | 5/2010 | Soler et al. |
| 7,942,663 B2 | 5/2011 | Ciccone |
| 7,942,896 B2 | 5/2011 | Anderhub et al. |
| 8,840,543 B2 | 9/2014 | Neal |
| 2006/0242813 A1 | 11/2006 | Molz et al. |
| 2008/0147120 A1 | 6/2008 | Molz et al. |
| 2008/0295312 A1 | 12/2008 | Molz et al. |
| 2012/0029564 A1 | 2/2012 | Trieu et al. |
| 2013/0012773 A1 | 1/2013 | Kwan |
| 2017/0035271 A1 | 2/2017 | Kwan |

OTHER PUBLICATIONS

Technical Information—DuPont(TM) Delrin(R) Acetal Resin molding Guide; 2006; 48 pages.
Mold Plastic Set Textbook for Website, Jetro Supporting Industry Program; Jun. 2006; 98 pages.

POLYMERIC MATERIAL FOR USE IN AND WITH STERILIZABLE MEDICAL DEVICES

CROSS-REFERENCE TO RELATED APPLICATION

This application is a Division of U.S. patent application Ser. No. 14/614,095, filed Feb. 4, 2015.

FIELD OF THE INVENTION

The present invention is generally related to a method of manufacturing medical device components, more particularly, to a method of manufacturing medical grade polymeric knob assemblies for use in endoscopic video cameras.

BACKGROUND OF THE INVENTION

Endoscopes and endoscopic video cameras are now widely used by physicians during surgery to view inside body cavities. Typically, the endoscopic video camera contains an optical focusing lens, an optical zoom lens, and a focus and zoom device that can be adjusted to optimize images transmitted by the endoscope. After each use with a patient, the endoscope and endoscopic video camera must be cleaned and sterilized before they can be used again. Due to cost and time considerations, it is desirable to sterilize both endoscopes and endoscopic video cameras using high temperature steam autoclaving.

The focus and zoom device usually includes external adjuster assemblies (e.g. a focusing knob assembly and a zoom knob assembly), and usually utilizes magnetic drives to move or rotate the optical focusing lens and the optical zoom lens. In an effort to simplify the focus and zoom device, and to solve various shortcomings associated with complicated endoscopic video cameras in the prior art, U.S. Pat. Nos. 6,522,477 and 6,633,438, both issued to Anhalt, disclose endoscopic video cameras having at least one magnetizable lens that moves or rotates in response to the rotation of an external magnetic adjuster assembly. The external magnetic adjuster assemblies of Anhalt have the following components and structures, as illustrated in FIG. 1. An adjuster assembly 10 includes an adjuster (i.e. a knob) 11 having grooves 12 on its inside diameter, magnetic spacers 13, 14, and o-rings (not shown). The adjuster 11 carries magnets 15, which are positioned axially and radially by the grooves 12 and by the magnetic spacers 13, 14. The o-rings provide tension to hold the adjuster 11 in place between adjustments, while also easing the rotation of the adjuster 11 by hand. The adjuster 11 is metallic, preferably made of stainless steel.

FIG. 2 illustrates an alternative embodiment of a prior art external adjuster assembly, which is a zoom knob assembly for an endoscopic camera. In this embodiment, zoom knob assembly 20 has a hollow metallic outer zoom knob (i.e. adjuster) 21, a metallic inner ring 22, a spacer ring 23, and an internal o-ring 24. Outer zoom knob 21 has bosses 25, an interior surface 26, and a floor 27 joining bosses 25 and interior surface 26. Outer zoom knob 21 carries external magnets 28, which are positioned axially and radially by the grooves 29 in inner ring 22. Inner ring 22 is positioned between the bosses 25 and the interior surface 26 of outer zoom knob 21.

Traditionally, the external adjusters 11 and 21, spacers 23, and metallic inner ring 22 of FIGS. 1 and 2 are manufactured from solid metal bar stocks by 100% machining. After machining, the external adjusters and spacer rings are two-step anodized to a particular color according to the product requirements. Additionally, the assembly of the external adjuster assemblies of FIGS. 1 and 2 requires press fits between their respective components and structures. For example, referring to FIG. 2, zoom knob assembly 20 requires press fits between outer zoom knob 21 and the inner ring 22, and press fits between the spacer ring 23 and inner ring 22. The design and method of manufacturing these prior art external adjuster assemblies unavoidably results in high manufacturing costs in terms of the cost and amount of the metal used, machining time, anodizing costs, assembly time, and inspection time. Also, using this manufacturing method, it is difficult, if not impossible, to machine the external adjuster assemblies with consistent precision.

In recent years, metal injection molding ("MIM") processes have been used to manufacture various components of medical or optical instruments, as disclosed in U.S. Pat. Nos. 6,514,269 and 7,718,100; and U.S. Pat. Appln. Nos. 2013/0012773 and 2006/0242813. The teachings of these references are incorporated herein by reference in their entirety. Compared to the traditional 100% machining and other techniques such as casting, stamping, and lithography, the MIM process reduces the amount of material used for manufacturing and allows a high volume production with reasonable consistency in quality. The MIM process is also versatile at producing small components having complex internal and external shapes.

One disadvantage of MIM processes is that they can require the application of several hundred tons of pressure to a mold, which results in high tooling costs. Additionally, the metal blanks that are used in the MIM processes are expensive and usually require a significant amount of "secondary machining" or "post machining" to achieve the desired high-precision dimensions of the final components. This manufacturing method therefore results in extremely high manufacturing costs for manufacturing external adjuster assemblies.

As an alternative to MIM processes, plastic injection molding ("IM") processes have been used to manufacture various polymeric components of medical devices, as disclosed in U.S. Pat. No. 7,942,896 and U.S. Pat. Appln. No. 2006/0242813. Typically, plastic components are less costly than metal components. However, one problem with plastic injection molding processes is that they may leave undesirable molding characteristics on the outer cosmetic surfaces of the final product, such as visible flow marks, weld lines, knit lines, gate marks, sink marks, and ejection pin marks. Additionally, during the assembly of plastic components, an undesired layer of material, also known as "flash," may escape to the outer cosmetic surfaces of the final product, and flash removal may be costly. Further, the cosmetic appearance of plastic components is typically not as visually appealing as metallic components, and polymeric components may have the tendency to degrade under high temperature steam autoclave sterilization.

What is needed, therefore, is an improved method of manufacturing medical device components, such as a zoom knob assembly or a focus knob assembly for an endoscopic camera, which utilizes plastic materials, shortens the overall manufacturing time, reduces the overall manufacturing cost, minimizes undesirable molding characteristics on the outer cosmetic surfaces of the components, and eliminates the need for flash removal. It is also desirable that the polymeric material used in such manufacturing method has a metallic appearance and withstands sterilization without showing signs of degrading. It is also desirable that such manufacturing method and polymeric material are sufficiently versatile to be applied to various types of medical device components.

SUMMARY OF THE INVENTION

The present invention provides methods of manufacturing a knob assembly and an endoscopic video camera having at least one knob assembly. The method comprises the steps of molding first and second plastic blanks using a plastic injection molding process, wherein the first plastic blank has a shell, an interior surface, an exterior surface, a first end, a second end, a sprue, a center web, at least one rib extending from the interior surface, a floor adjoining the interior surface at the second end, at least one boss extending from the floor, and a groove on the interior surface at the first end, and wherein the second plastic blank has a sprue, a center web having at least one recess, and a skirt; trimming the sprues of the first and second plastic blanks; machining an o-ring pocket into the first plastic blank; inserting a ring into the first plastic blank; inserting magnets into the ring; spin-welding the second plastic blank to the first plastic blank to form the knob assembly, which covers at least a portion of the ring; machining an o-ring pocket and a stop groove into the second plastic blank of the knob assembly; machining the exterior surface of the knob assembly; laser marking the knob assembly using a green laser process; and assembling the knob assembly into an endoscopic camera.

One aspect of the invention is that the step of spin-welding the second plastic blank to the first plastic blank creates a shear welded joint having a shutoff path that traps flash, thereby preventing it from tarnishing the outer cosmetic surface of the knob assembly.

In a second embodiment, the methods of manufacturing a knob assembly and an endoscopic video camera having at least one knob assembly comprise forming first and second metal blanks using a metal injection molding process, wherein the first metal blank comprises a ring having a first end, a second end, an outside diameter, an inside diameter, at least one groove on its inside diameter, a stop groove on its first end, and at least one boss extending from its outside diameter, and the second metal blank comprises a ring having an outside diameter, an inside diameter, and a skirt extending from said inside diameter of said second metal blank; assembling the first and second metal blanks to form an inner ring; over-molding the inner ring with a plastic material using a plastic injection molding system to form a knob assembly; post-machining the knob assembly; inserting magnets into the inner ring; laser-marking the knob assembly using a green laser process; and assembling the knob assembly into the camera.

In a preferred embodiment, the first and second metal blanks of the second embodiment are assembled by a co-sintering process.

One aspect of the invention is that in each embodiment, undesirable molding characteristics (e.g. flow lines, knit lines, burn marks, and splay) are located on the sprues, center webs and "sacrificial" portions of the plastic material where gating connections are made during the plastic injection molding process, and these structures are completely removed by secondary machining or post machining during subsequent steps of manufacturing method. This minimizes or eliminates the occurrence of undesirable molding characteristics on the outer cosmetic surfaces of the knob assemblies.

Preferably, the plastic material used in the manufacturing of the knob assemblies of the invention comprises 99-100% polyphenylsulfone resin, 0.1-1% mica, 0.01-0.1% titanium dioxide, up to 0.01% tin oxide, 0.01-0.1% solvent blue 104, and 0.01-0.1% solvent violet 13. This unique plastic material gives the knob assemblies a metallic color to mimic and match the appearance of anodized metallic knobs, is capable of withstanding sterilization without showing any signs of degrading or fading of color, and it is versatile enough to be used in the manufacturing of various different medical device components, such as zoom knob assemblies, focus knob assemblies, and camera head sleeves. This is yet another aspect of the present invention.

DETAILED DESCRIPTION OF THE INVENTION

The present invention provides a method of manufacturing an endoscopic video camera having one or more external adjuster assemblies, such as a zoom knob assembly or a focus knob assembly.

Figure 1:
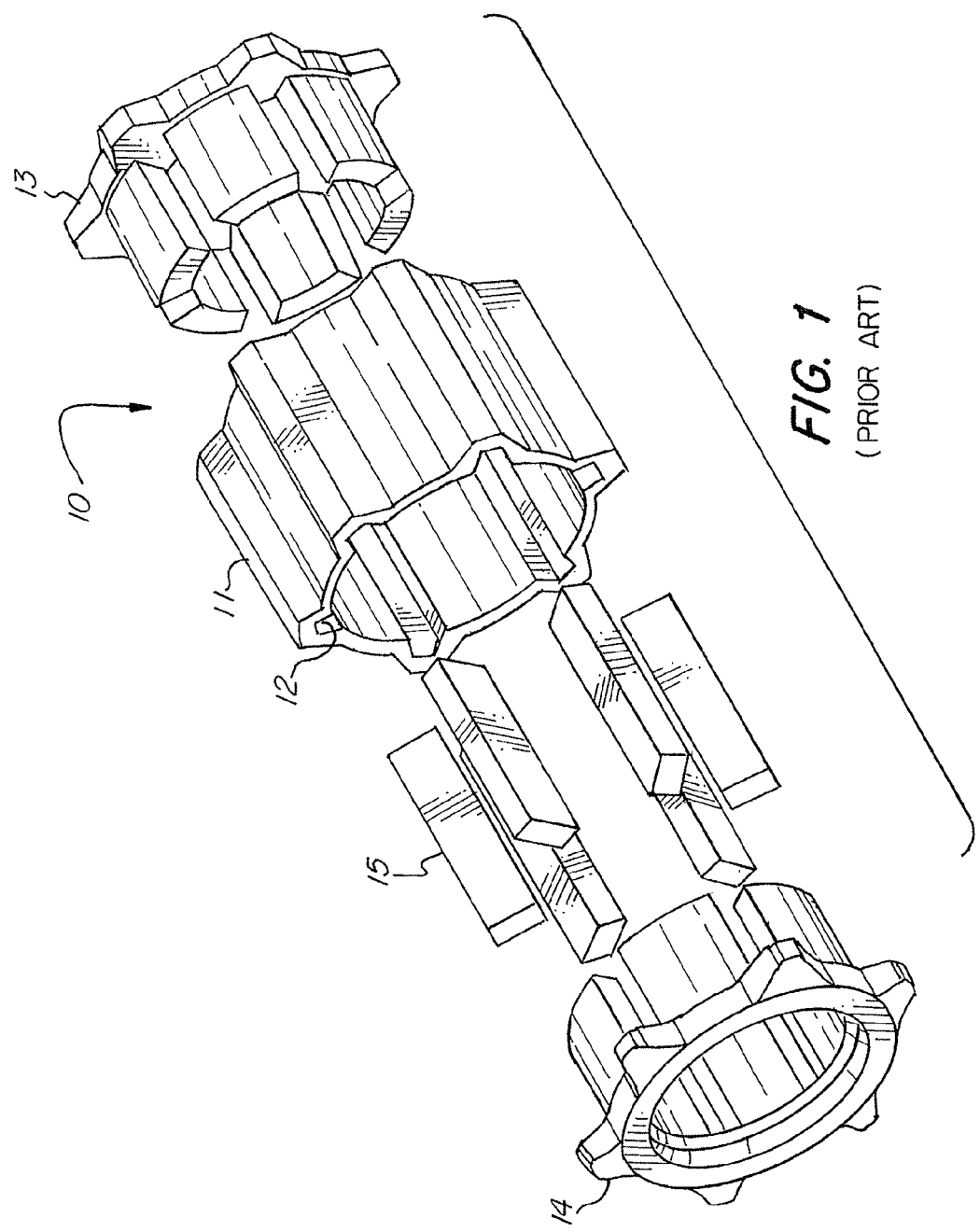
FIG. 1 illustrates a knob assembly as disclosed in prior art U.S. Pat. Nos. 6,522,477 and 6,633,438 to Anhalt.
Figure 2:
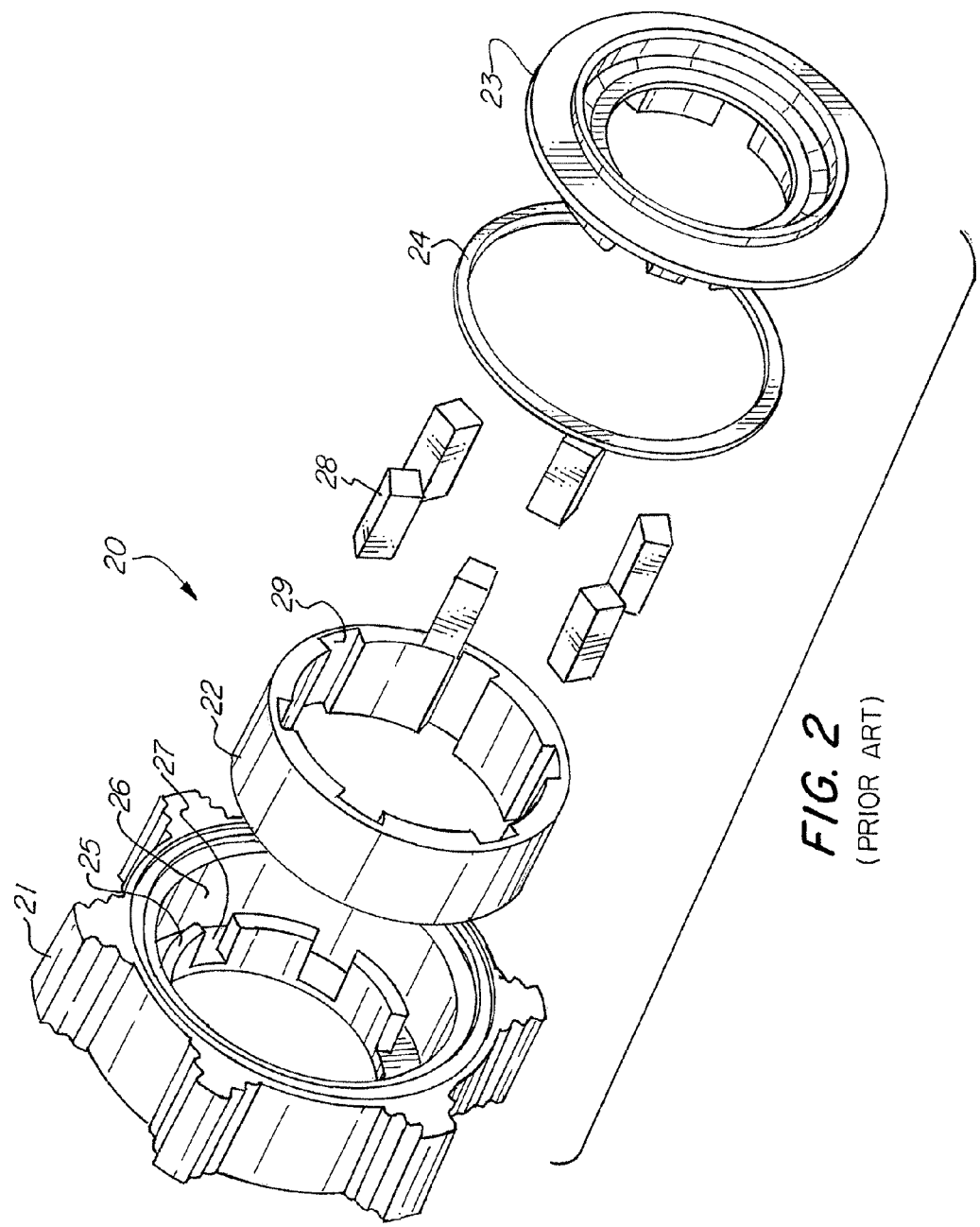
FIG. 2 illustrates another prior art knob assembly.
Figure 3:
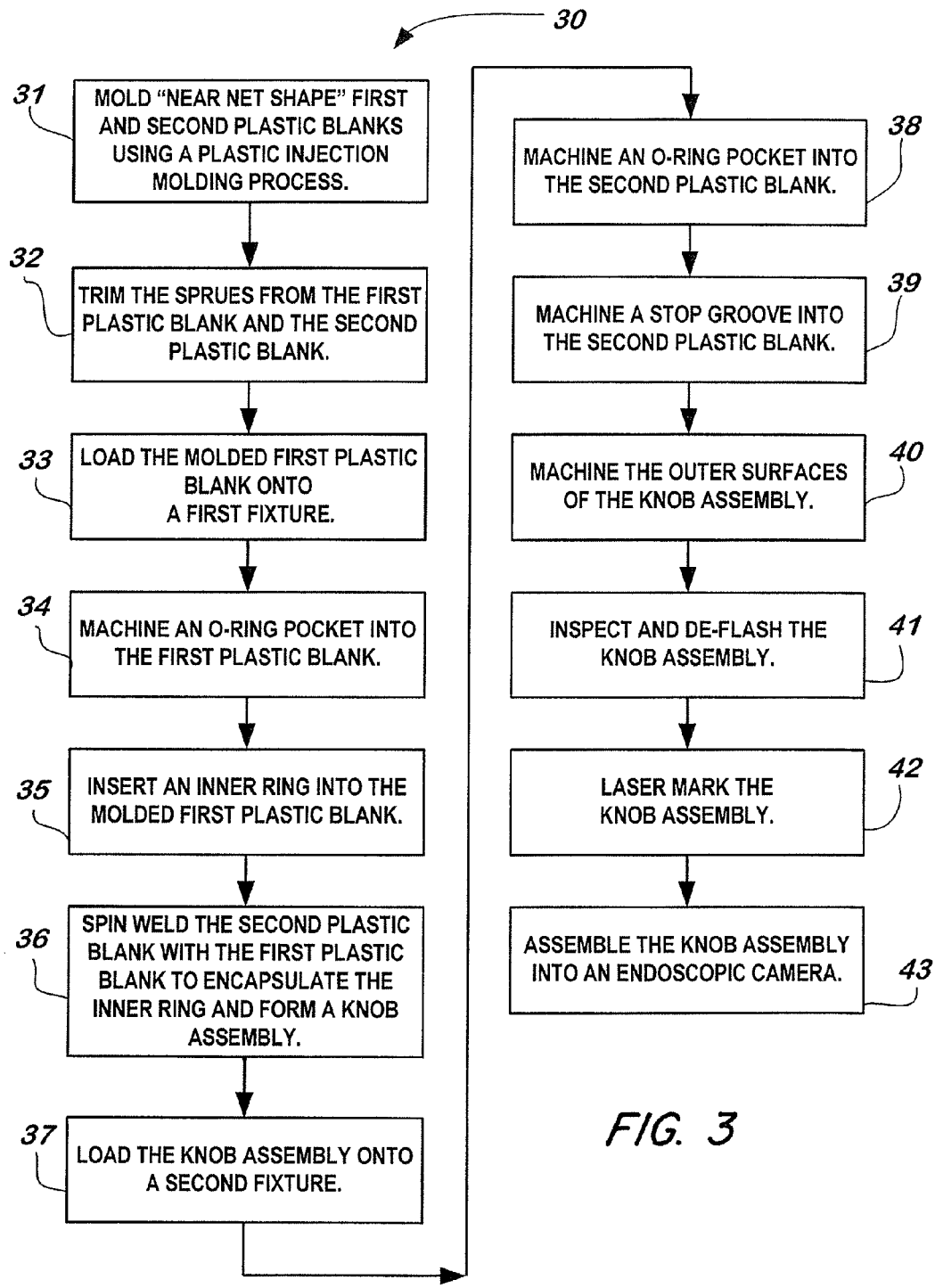
FIG. 3 illustrates various steps of the manufacturing method in accordance with the first embodiment of the invention.

FIG. 3. illustrates various steps of the manufacturing method 30 in accordance with the first embodiment of the present invention. Manufacturing method 30 utilizes a near net machining concept. Under this concept, a plastic or metal blank, which includes all molding features (e.g. gating system, sprue) is first molded by a plastic injection molding (IM) process or a metal injection molding (MIM) process to a "near net shape" of the final component such that minimal secondary machining is required to meet the specification of, for example, a final component such as a plastic zoom knob or a metallic inner ring for an endoscopic video camera.

The term "IM process" refers to the process which uses plastic material, a hollow mold, and an injection molding machine to manufacture plastic components. Typically, the plastic is melted in the injection molding machine and then injected into the mold, where it cools and solidifies into the plastic component. The IM process is a superior process because it minimizes waste material and allows the simplified and low-cost mass production of complex and irregular shapes, and multiple parts can be simultaneously manufactured using the same mold. Injection molding machines are known in the art. Injection molding machines, the IM process, and examples of plastic materials for use therein have been described, for example, in U.S. Pat. Nos. 7,942,663, 7,452,201, and 7,942,896; and in U.S. Pat. Appln. Nos. 20080295312 and 20080147120, the disclosures of each of which are incorporated herein in their entirety.

The term "MIM process" refers to the process which combines metal powders with binder materials to produce a "feedstock" that is injected as a liquid into a hollow mold using injection molding machines, followed by the binder removal and the sintering step to solidify the molded metal component. The MIM process is also a superior process as compared to other processes such as forging or casting, in that it allows an arbitrary selection of the shape of the metal body, including irregular shapes, and in that it is suitable for mass production at a lower cost, and in that the sintered product has excellent physical and mechanical properties as a result of the improved compaction obtained by the use of fine powder. In addition, the MIM process can achieve tighter tolerances than other processes, e.g. casting, extrusion, or forging. The MIM process and the feedstock for use therein have been described, for example, in U.S. Pat. Nos. 4,694,881, 4,694,882, 5,040,589, 5,064,463, 5,577,546, 5,848,350, 6,860,316, 6,890,368, 6,838,046, 6,790,252, 6,669,898, 6,619,370, 6,478,842, 6,470,956, 6,350,328, 6,298,901, 5,993,507, 5,989,493, and 7,718,100; and in U.S. Pat. Appln. Nos. 20060242813, 20080147120, and 20080295312, the disclosures of each of which are incorporated herein in their entirety.

The term "machining" or "machined" refers to conventional surface treatments such as abrading, cutting, drilling, forming, grinding, and/or shaping a piece of material into the desired final piece by using machine tools such as lathes, power saws, and presses.

The first step 31 in manufacturing method 30 is molding "near net shape" first and second plastic blanks, each having a sprue and a center web, using a plastic injection molding process.

Figure 4A:
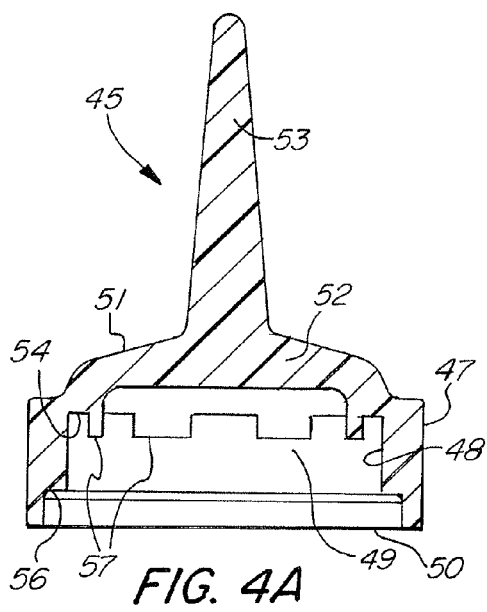
FIGS. 4A-4E, FIGS. 5A-5B, and FIGS. 6A-6B are cross sections of components of a knob assembly during various steps of the manufacturing method according to the first embodiment.
Figure 4B:
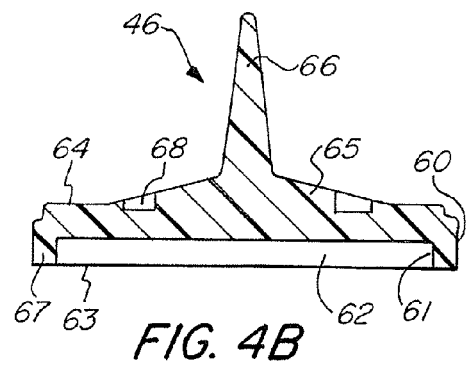
Figure 4C:
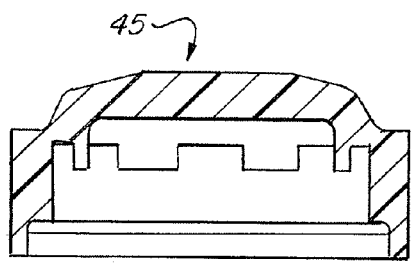

FIG. 4A illustrates a cross section of a "near net shape" first plastic blank 45 and FIG. 4B illustrates a cross section of a "near net shape" second plastic blank 46, during a manufacturing method 30 in accordance with the first embodiment of the present invention.

Figure 4D:
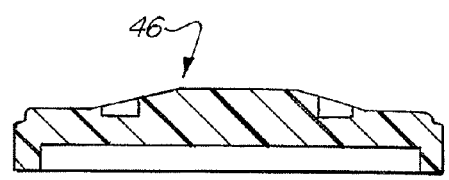
Figure 4E:
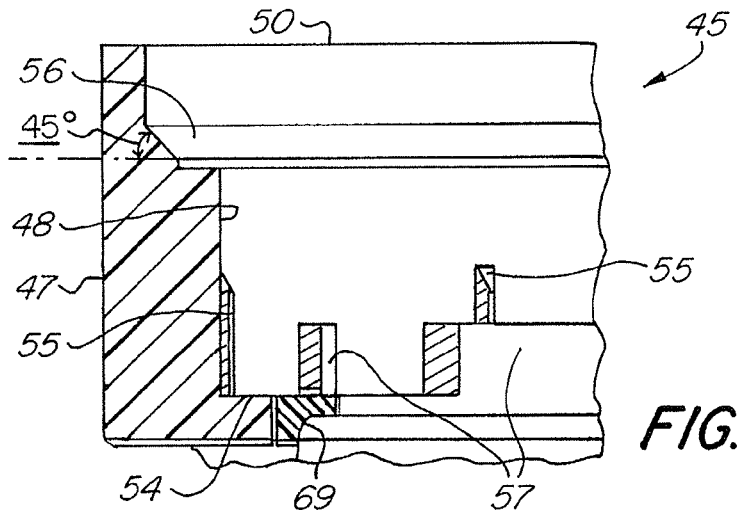
Figure 8:
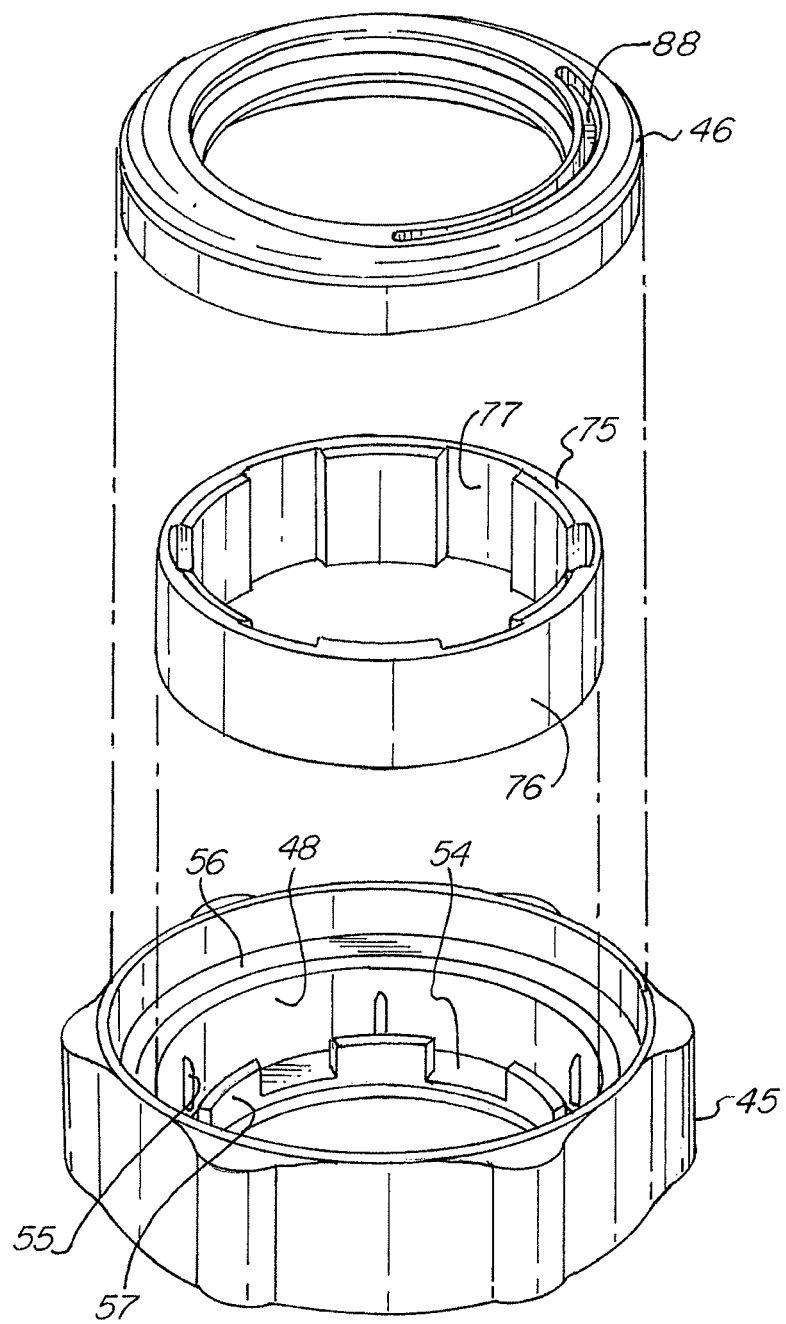
FIG. 8 is an exploded view of the components of the knob assembly shown in FIG. 7A.

Referring to FIGS. 4A, 4E and 8, first plastic blank 45 comprises a cylindrical shell that has an exterior surface 47 and an interior surface 48. Interior surface 48 defines a cavity 49, which is open at a first end 50 of first plastic blank 45, and closed at a second end 51 of first plastic blank 45 by center web 52 and sprue 53. First plastic blank 45 also has various additional structures, including crush ribs 55, bosses 57, and a floor 54 adjoining the interior surface 48 at second end 51. In a preferred embodiment, crush ribs 55 are evenly distributed along the interior surface 48, and bosses 57 are evenly distributed along floor 54. First plastic blank 45 also has a groove 56 in interior surface 48 at the first end 50. In a preferred embodiment, a portion of the cross-section of groove 56 has a 45 degree slope (refer to FIG. 4E), to facilitate the subsequent spin welding step of manufacturing method 30.

Referring to FIG. 4B, second plastic blank 46 comprises a shell that has an exterior surface 60 and an interior surface 61. Interior surface 61 defines a shallow cavity 62, which is open at a first end 63 of second plastic blank 46 and closed at a second end 64 of second plastic blank 46 by center web 65 and sprue 66. Second plastic blank 46 also includes a circumferential skirt 67. In a preferred embodiment, the center web 65 of second plastic blank 46 includes spin welding driving features 68, which are preferably two circular indentations or recesses in center web 65. Spin welding driving features 68 are used to facilitate the subsequent spin welding step of manufacturing method 30.

In a preferred embodiment, first and second plastic blanks 45 and 46 are each molded using a single diaphragm gate. This gating design provides various benefits such as avoiding the appearance of undesirable molding characteristics (e.g. flow lines, knit lines, burn marks, and splay) on the exterior surfaces 47 and 60 of first and second plastic blanks 45 and 46, because all undesirable molding characteristics are located on the center webs 52, 65 and the sprues 53, 66, which are completely removed by secondary machining during subsequent steps of manufacturing method 30.

The properties of the plastic materials used in an IM process determine the final properties of the IM product. Suitable plastic materials for molding first and second plastic blanks 45 and 46 of the present invention include, but are not limited to, polymeric materials such as polyphenylsufone resin (Radel). In a preferred embodiment, the plastic material used for molding first and second plastic blanks 45 and 46 of the present invention comprises a unique formulation of polyphenylsufone resin (Radel), which comprises of polyphenylsufone resin (Radel), mica, titanium dioxide, tin oxide, and colored metallic additives (e.g. solvent blue 104, and solvent violet 13). The colored additives give the preferred plastic material a metallic color to mimic and match the appearance of anodized metallic knobs. The preferred plastic material is also capable of withstanding heat autoclave sterilization without showing any signs of degrading or fading of color. An additional benefit of the preferred plastic material is that it can easily be injection molded, spin-welded, and machined to create the required features and dimensions of various medical device components, such as zoom knob assemblies, focus knob assemblies, and camera head sleeves.

In step 32 of manufacturing method 30, to facilitate subsequent manufacturing steps, sprues 53 and 66 are trimmed from first plastic blank 45 and second plastic blank 46. FIGS. 4O and 4D show first plastic blank 45 and second plastic blank 46 after the completion of step 32.

A person of ordinary skill in the art would understand that in step 31, first and second plastic blanks 45 and 46 can be molded simultaneously or in reverse order. Similarly, in step 32, the sprue 53 of first plastic blank 45 and sprue 66 of second plastic blank 46 can be trimmed simultaneously or in reverse order.

Figure 5A:
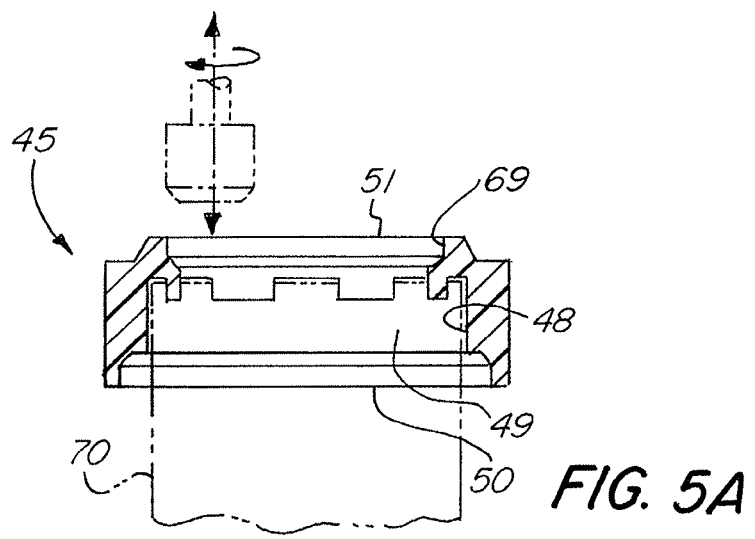

Referring to FIG. 5A, during the next steps 33 and 34, the first plastic blank 45 is loaded onto a fixture 70, and an o-ring pocket 69 is machined into the first plastic blank 45. During step 34, the center web 52 of first plastic blank 45 is also removed. Accordingly, as shown in FIG. 5A, after completion of step 34, the cavity 49 of first plastic blank 45 is open at a second end 51. O-ring pocket 69 is preferably a groove in the interior surface 48 at second end 51. O-rings and their function are described, for example, in U.S. Pat. No. 6,522,477.

In step 35 of manufacturing method 30, a metallic inner ring 75 is inserted into first plastic blank 45 (refer to FIGS. 5B and 8) and positioned on the floor 54 of first plastic blank 45 between crush ribs 55 and bosses 57. The function of the crush ribs 55 of first plastic blank 45 is to align the inner ring 75 inside the first plastic blank 45, and to generate an interference fit between the interior surface 48 of first plastic blank 45 and the outside diameter 76 of the metallic inner ring 75, thereby preventing inner ring 75 from moving or vibrating during subsequent steps in the manufacturing method 30. Suitable metals for the inner ring of the current invention include, but are not limited to, stainless steel and aluminum. The preferred metal for the inner ring is aluminum. The inner ring can be manufactured by metal powder sintering technology, MIM technology, or die casting technology, each of which is known in the art, to reduce high machining costs. The preferred method of manufacturing the inner ring of the current invention is a MIM process.

Figure 5B:
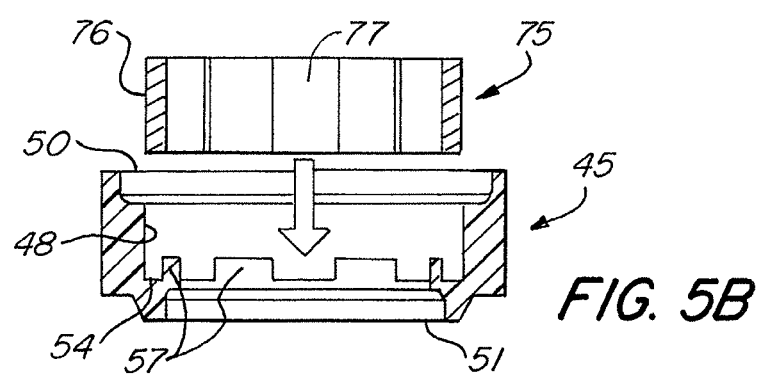

Inner ring 75 has longitudinal grooves 77 which are preferably located in its inside diameter (refer to FIG. 5B and FIG. 8). In a preferred embodiment, after step 35, magnets (not shown) are positioned axially and radially in the grooves 77 of inner ring 75, to facilitate the focus or zooming operations of a focus or zoom knob assembly manufactured according to the present invention when assembled into an endoscopic camera. The purpose and function of such magnets is disclosed, for example, in U.S. Pat. No. 6,522,477, which is incorporated herein by reference in its entirety.

Figure 6A:
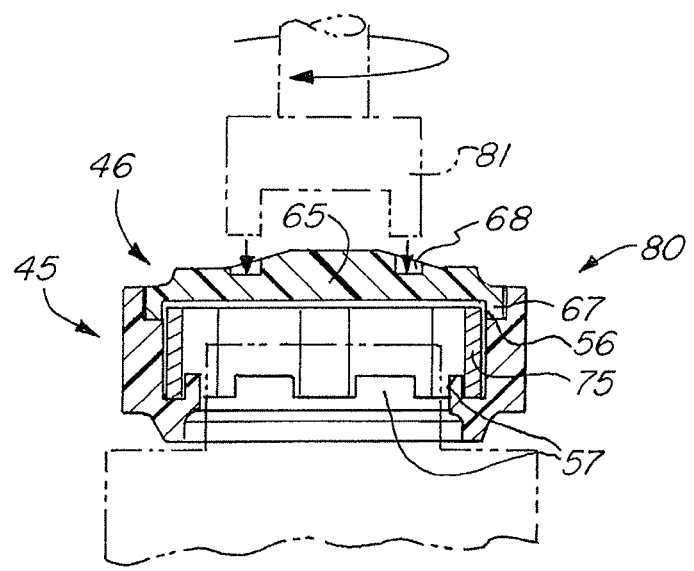

In step 36, the second plastic blank 46 is spin-welded to the first plastic blank 45 to form a knob assembly that encapsulates the inner ring. FIG. 6A shows a cross-section of knob assembly 80 during the spin welding step. The skirt 67 of second plastic blank 46 is located on the groove 56 of first plastic blank 45 in preparation for the spin welding process. In a preferred embodiment, the skirt 67 has a "tongue" design to allow the second plastic blank 46 to fit into the first plastic blank and generate a 45 degree shear welded joint between the first and second plastic blanks 45 and 46. The initial point of contact of the second plastic blank 46 to the first plastic blank 45 is at the corner of the tongue to initial melting of the plastic material during the spin welding process.

Referring to FIG. 6A, during step 36, inner ring 75 is encapsulated between the second plastic blank 46 and the first plastic blank 45, and it is aligned and constrained by crush ribs 55 (not shown) and bosses 57 to prevent movement during the spin welding process and subsequent steps in the manufacturing method. Spin welding driving tool 81 uses spin welding driving features 68 to facilitate the spin welding process. A person of ordinary skill in the art would understand that the dimensions of the spin welding driving features can be varied based on the specifications of the driving tool 81.

In a preferred embodiment, during the spin welding process there is approximately a 0.75 mm collapse distance between the first and second plastic blanks 45, 46 to produce a shear welded joint with the required strength and seal. The collapse distance is controlled by the number of revolutions of the second plastic blank 46, which can be set by a person of ordinary skill in the art. The resolution of the revolution achieved by the spin welding machine is within 5 degrees, which is equivalent to 0.0035 mm of the required vertical displacement.

Figure 6B:
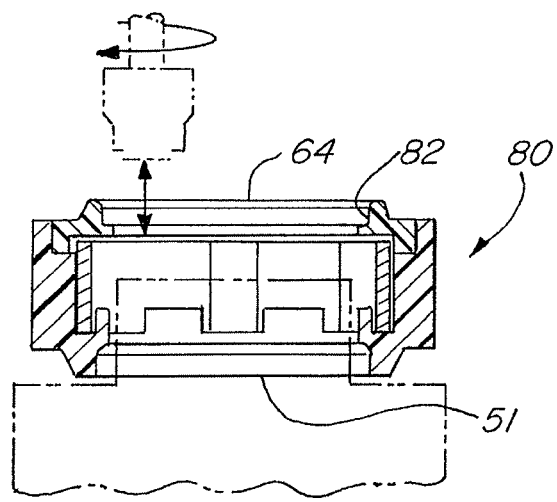

In steps 37-38, the knob assembly 80 is loaded onto a fixture, and an o-ring pocket 82 is machined into the second plastic blank 46 of knob assembly 80. During step 38, the center web 65, including spin welding driving features 68, of second plastic blank 46 is also removed. Accordingly, as shown in FIG. 6B, after completion of step 38, the knob assembly 80 is open at first end 51 and second end 64. O-ring pocket 82 is preferably a circumferential groove in the second plastic blank 46 at second end 64 of knob assembly 80.

Figure 7A:
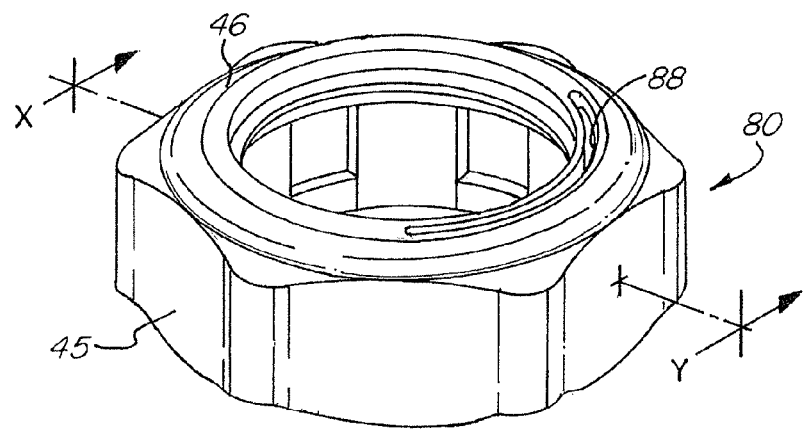
FIG. 7A is a perspective view of a knob assembly according to the first embodiment.
Figure 7B:
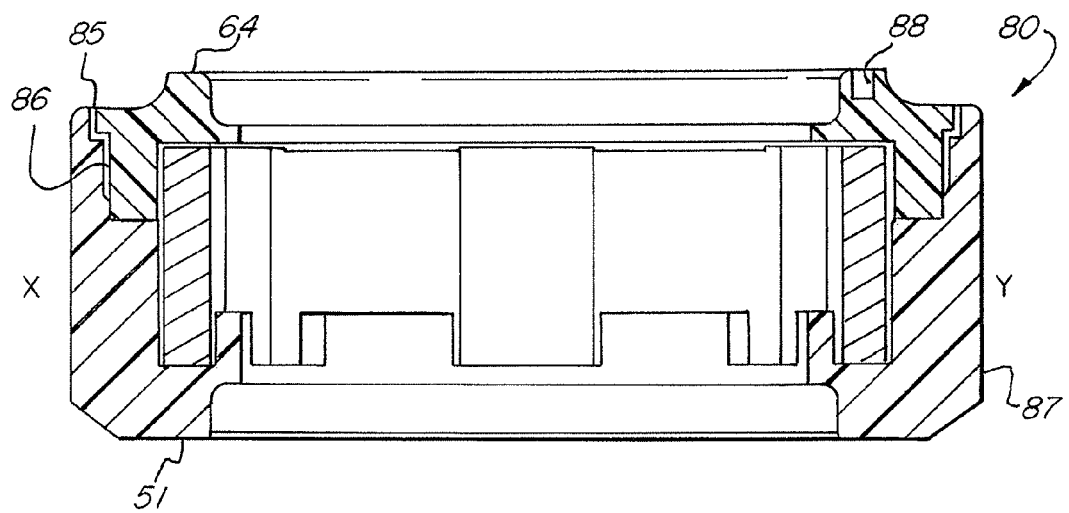
FIG. 7B is a cross-sectional side view of the knob assembly shown in FIG. 7A.

In step 39, a stop groove is machined into the knob assembly. The function of the stop groove in to prevent over-rotation of the knob assembly when it is being used in a medical device such as an endoscopic camera. Referring to FIGS. 7A and 7B, stop groove 88 is machined into the second plastic blank 46 at second end 64 of knob assembly 80. In step 40, the outer surface 87 of the knob assembly 80 is machined to achieve the required outer dimensions of the knob assembly, such as the height.

Referring to FIG. 7B, knob assembly 80 includes spin welded joint 85, which is created during the spin welding step 36 of manufacturing process 30. The spin welded joint 85 has a unique "shutoff" path 86, which helps to contain flash that is generated during the manufacturing process and thereby reduces or eliminates the presence of flash on the outer surface 87 of the knob assembly 80. The spin welded joint 85 entraps 90%-100% of flash generated during the spin weld step of manufacturing method 30, and therefore reduces or eliminates the need for de-flashing the outer surface 87.

The next step 41 is optional for the manufacturing method 30 in accordance with the present invention. In this step 41, the outer surface 87 of the knob assembly 80 is inspected. If flash is discovered on the outer surface 87 during the inspection, it is removed using a de-flashing process.

In the next step 42, the knob assembly is laser marked. The term "laser marked" or "laser marking" refers to the process of engraving the assembly with marks that assist an end user in identifying the functionality of the assembly, such "+" or "−" marks that identify the rotational direction of the knob assembly for zooming out or in on images. Preferably, a green laser process is used to laser mark the knob assembly. Less preferably, a CO2 process can be used to laser mark the knob assembly.

Figure 9:
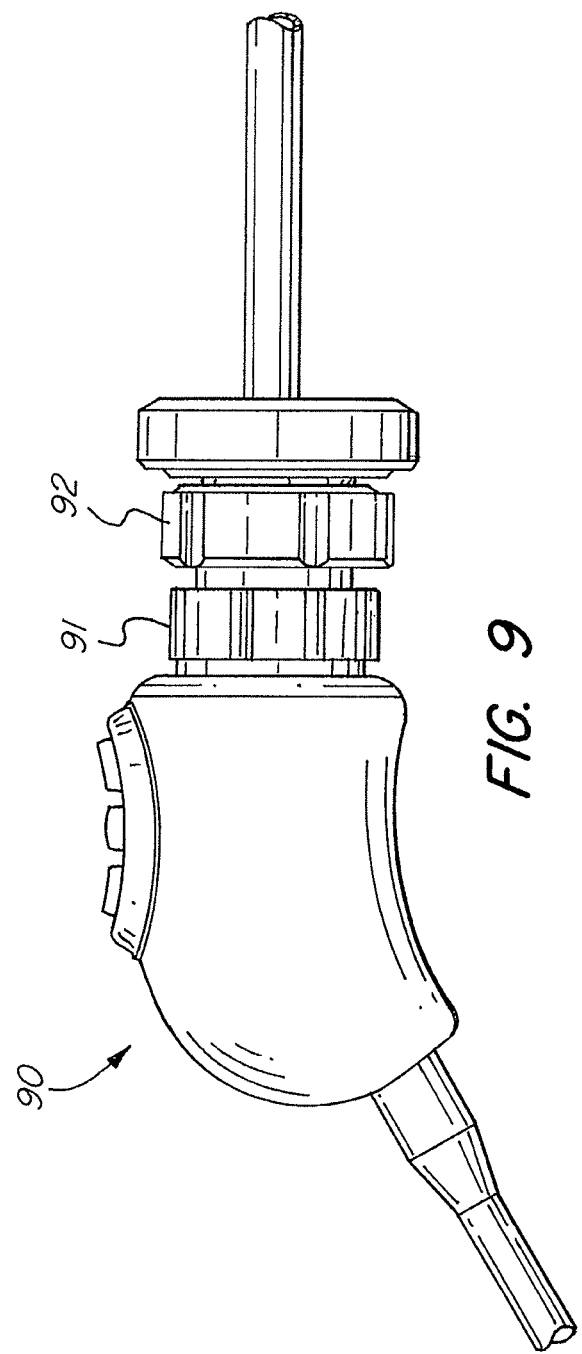
FIG. 9 is a side view of an endoscopic video camera head.

In the final step 43 of manufacturing method 30, the knob assembly 80 is assembled into an endoscopic video camera. A person with ordinary skill in the art would understand that, in the event that an endoscopic video camera requires more than one knob assembly, each knob assembly can be manufactured in accordance with the same or different embodiments of the present invention. For example, FIG. 9 shows a focus knob assembly 91 and a zoom knob assembly 92 manufactured according the present invention assembled into the camera head 90 of an endoscopic video camera.

Figure 10:
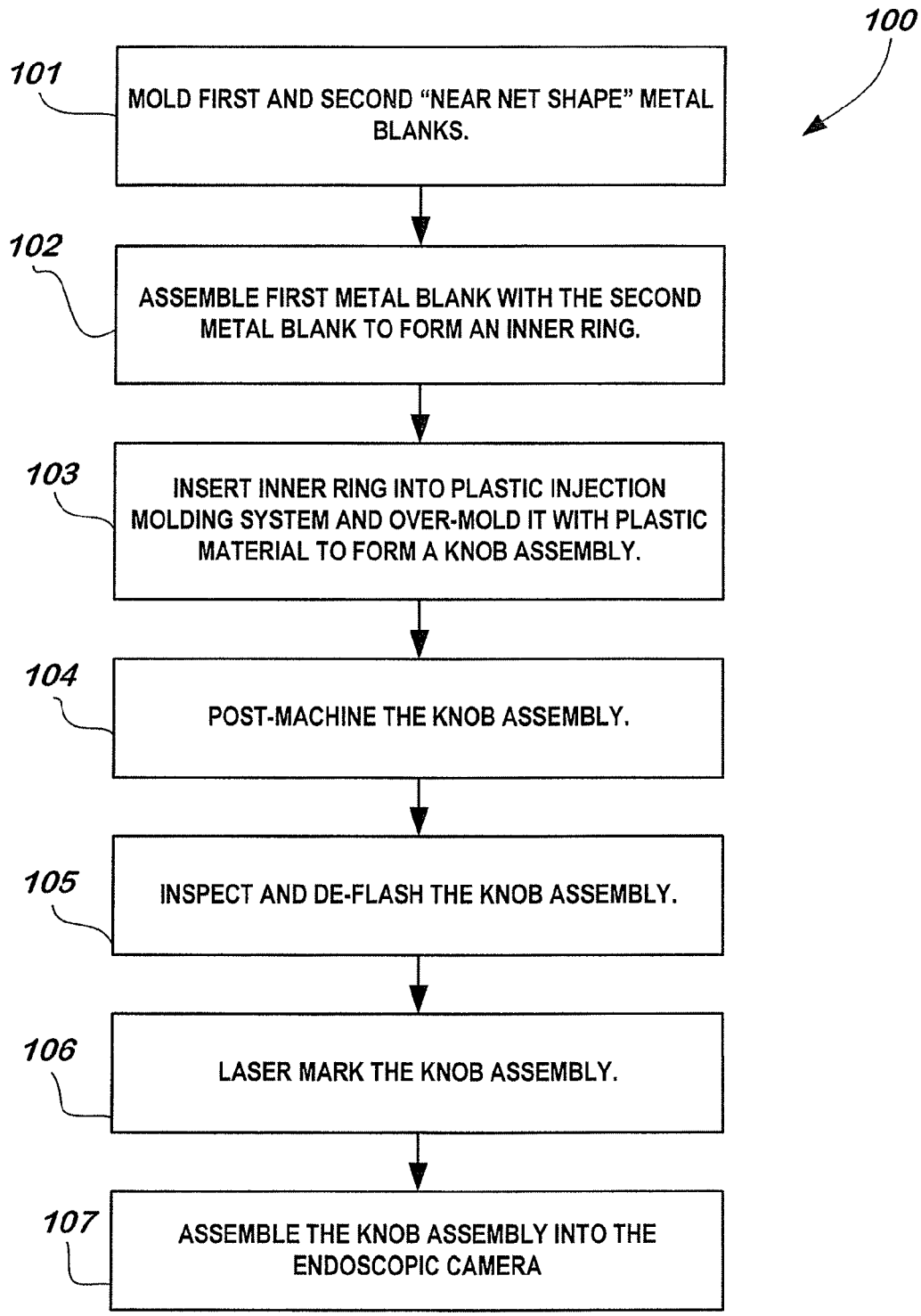
FIG. 10 illustrates various steps of the manufacturing method in accordance with a second embodiment.

FIG. 10 illustrates various steps of manufacturing method 100 in accordance with the second embodiment of the present invention. Similar to the first embodiment, manufacturing method 100 uses a near net machining concept.

The first step 101 in manufacturing method 100 is molding first and second "near net shape" metal blanks. The first and second metal blanks can be manufactured by metal powder sintering technology, MIM technology, or die casting technology, each of which is known in the art, to reduce high machining costs. The preferred method of manufacturing the first and second metal blanks of the present embodiment is a MIM process. Suitable metals for use in manufacturing the first and second metal blanks of the present embodiment include, but are not limited to, stainless steel and aluminum. The preferred metal for the first and second metal blanks of the present embodiment is aluminum.

Figure 12:
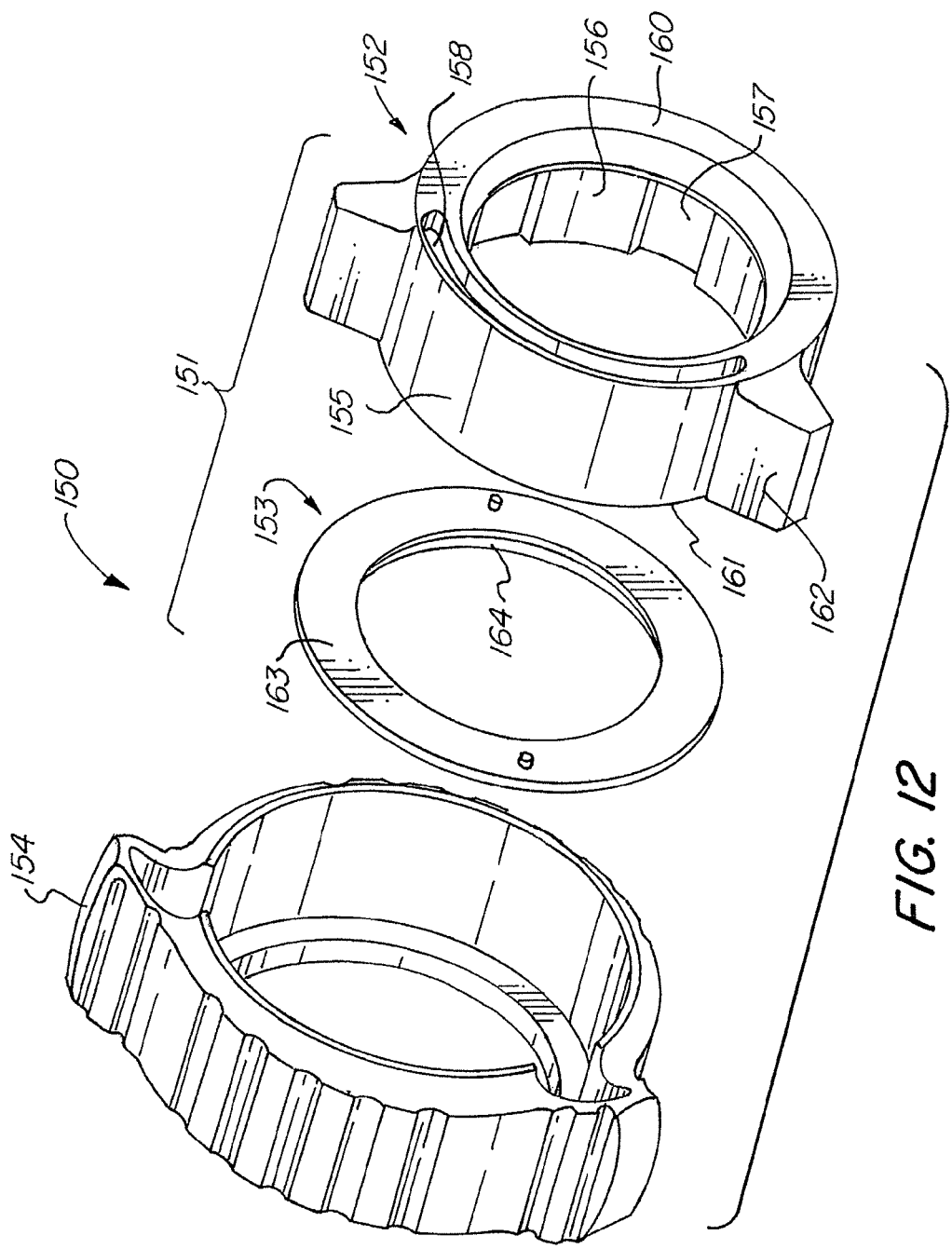
FIG. 12 is an exploded view of the components of the knob assembly shown in FIG. 11B.
Figure 13:
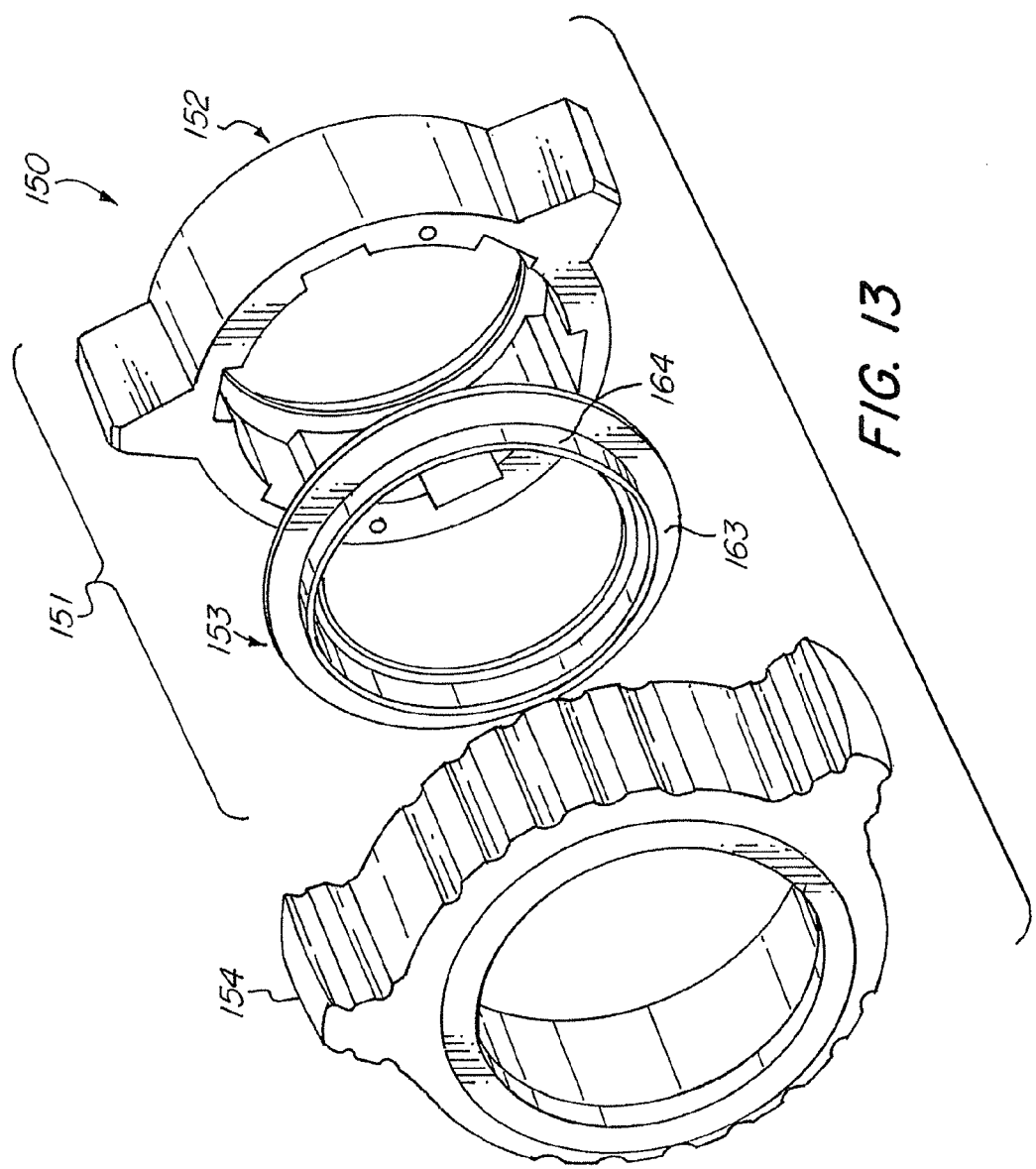
FIG. 13 is an exploded aerial view of the components of the knob assembly shown in FIG. 11A.

Referring to FIGS. 12 and 13, first metal blank 152 comprises a cylindrical ring that has an outside diameter 155 and an inside diameter 156. First metal blank has longitudinal grooves 157 which are located in its inside diameter 156. First metal blank further has a stop groove 158 on its first end 160, and two external bosses 162 on its outer diameter. Second metal blank 153 comprises a flat circular ring 163 with a cylindrical skirt 164 along its inner diameter.

Figure 14:
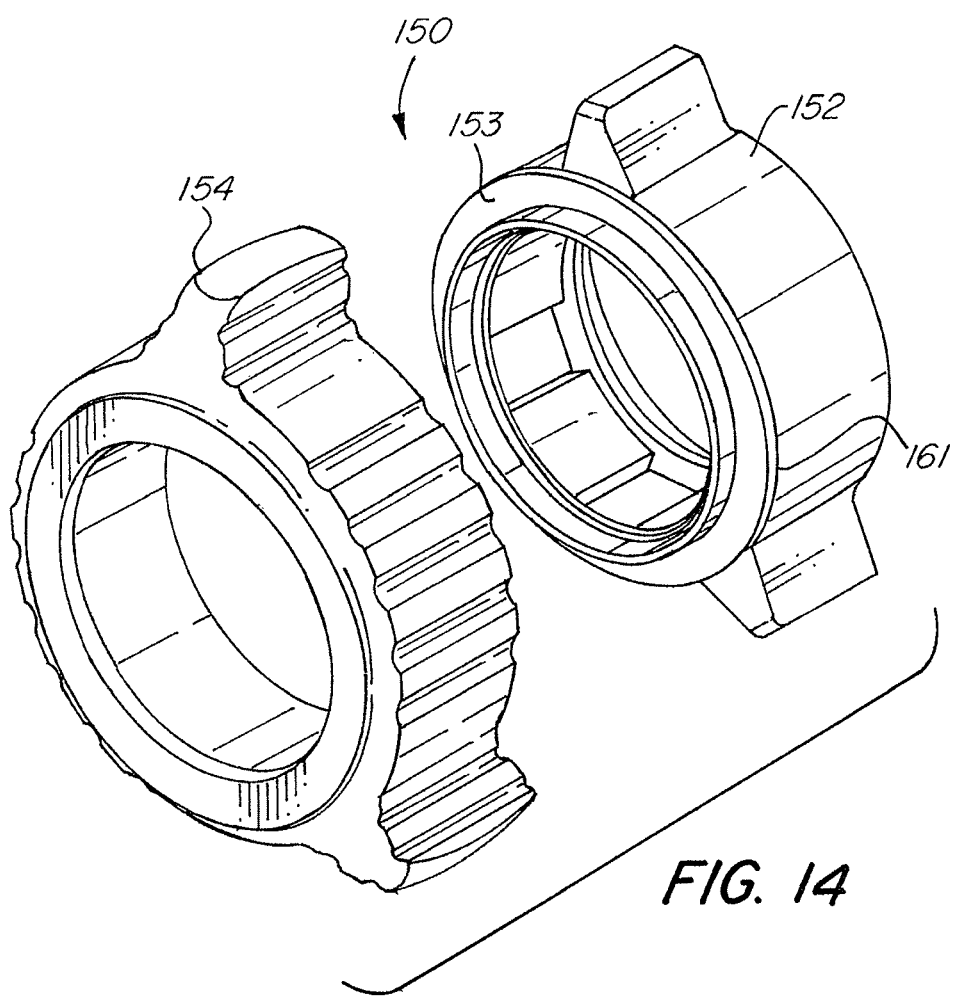
FIG. 14 is a second exploded aerial view of the components of the knob assembly shown in FIG. 11A.

In step 102, first metal blank 152 and second metal blank 153 are assembled into one piece through co-sintering, mechanical fit, or bonding processes, to form a metal inner ring 151. As illustrated in FIG. 14, during step 102, second metal blank 153 is assembled to a second end 161 of first metal blank 152. In a preferred embodiment, the first and second metal blanks are assembled through co-sintering. The design of the present embodiment, which divides the metal inner ring into two separate components, provides the advantage of simplifying the sintering, molding, or casting processes that are used for manufacturing the metal inner ring of the present invention.

In step 103, the assembled metal inner ring 151 is inserted into a plastic injection molding system and over-molded with a plastic material to form a knob assembly. Similar to the first embodiment, suitable plastic materials for over-molding the inner ring include, but are not limited to, polymeric materials such as polyphenylsufone resin (Radel). Likewise, in a preferred embodiment, the plastic material used for over-molding comprises a unique formulation of polyphenylsufone resin (Radel), which comprises of polyphenylsufone resin (Radel), mica, titanium dioxide, tin oxide, and colored metallic additives (e.g. solvent blue 104, and solvent violet 13). The colored additives give the preferred plastic material a metallic color to mimic and match the appearance of anodized metallic knobs. The preferred plastic material is also capable of withstanding heat autoclave sterilization without showing any signs of degrading or fading of color. An additional benefit of the preferred plastic material is that it can easily be injection molded and machined to create the required features and dimensions of various medical device components, such as zoom knob assemblies, focus knob assemblies, and camera head sleeves.

In a preferred embodiment, the over-molding step is performed using a multiple gating system. A multiple gating system can facilitate the uniform filling of the mold cavity. It can also minimize undesirable molding characteristics (e.g. flow lines, flow marks, knit lines) on the exterior surface areas of the knob assembly by concentrating them on the portion of the knob assembly where the gating connections are made during the over-molding process (e.g. on a "sacrificial ring" of plastic material used for the over-molding process). That portion (e.g. the "sacrificial ring") is completely removed by post machining, secondary machining or trimming in subsequent steps of manufacturing method 100, to leave minimal undesired marks on the knob assembly.

Figure 11A:
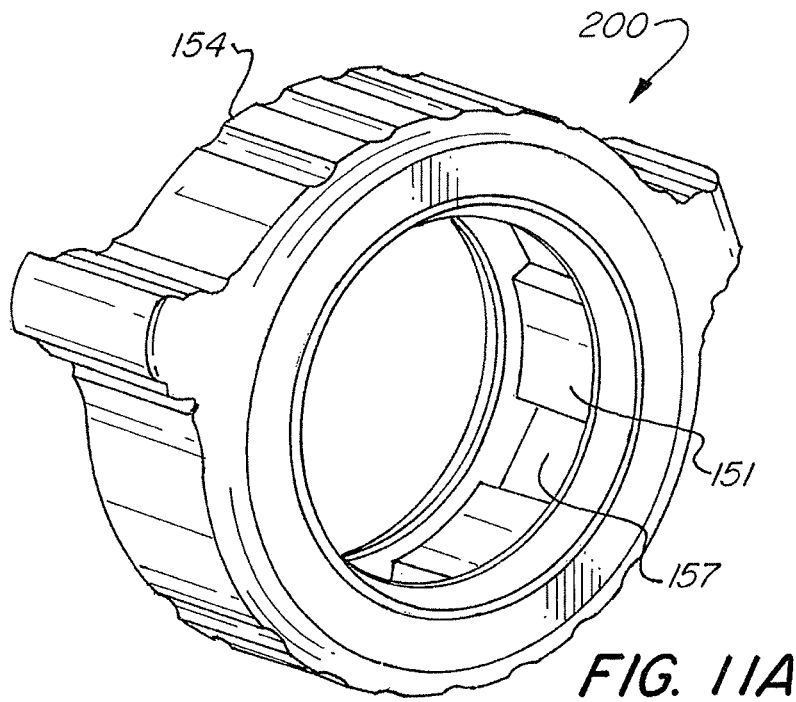
FIG. 11A is an aerial perspective view of a knob assembly according to the second embodiment.
Figure 11B:
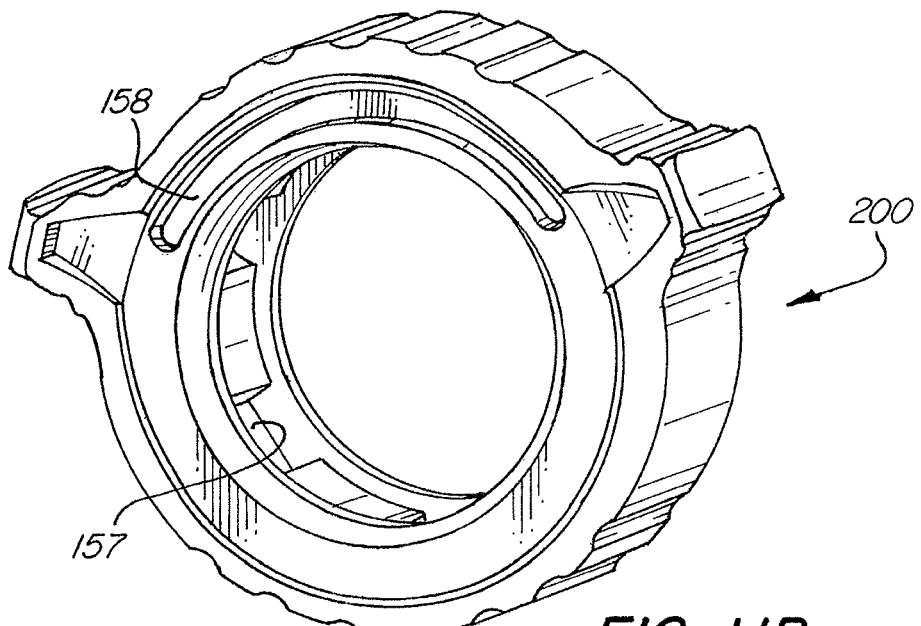
FIG. 11B is a worm's eye perspective view of the knob assembly shown in FIG. 11A.

In step 104, knob assembly 200 is post-machined to achieve and/or expose the required outer dimensions and features of the knob assembly. For example, the knob assembly 200 is post-machined to remove the portion of the knob assembly where the gating connections are made during the over-molding process (e.g. the "sacrificial ring"). FIGS. 11A and 11B illustrate a knob assembly 200 after the completion of step 104. Knob assembly 200 comprises inner ring 151, and cylindrical shell 154 which was molded around inner ring 151 during the over-molding step and encapsulates at least a portion of inner ring 151.

The next step 105 is optional for the manufacturing method 100. In this step, the shell 154 of knob assembly 200 is inspected, and if flash is discovered on shell 154 during the inspection, it is removed using a de-flashing process.

In step 106, the knob assembly is laser marked in a similar manner as the first embodiment, preferably using a green laser process. Less preferably, a CO2 process can be used to laser mark the knob assembly of the present embodiment.

In the final step 107 of manufacturing method 100, the knob assembly 200 is assembled into an endoscopic video camera. A person of ordinary skill in the art would understand that, in the event that an endoscopic video camera requires more than one knob assembly, each knob assembly can be manufactured in accordance with the same or different embodiments of the present invention.

One advantage of the present embodiment is that it transfers all precision features from the shell 154 of the knob assembly 200 to the inner ring 151, resulting in significant reduction in material and manufacturing costs (at least $100 savings per knob assembly), and it also reduces machining and inspection time and costs. For example, it eliminates the need to mold features (e.g. crush ribs and bosses) into the knob assembly's shell for aligning and securing the inner ring inside the shell. The present embodiment also allows for ease of insertion and removal of magnets (not shown) from the grooves 157 of inner ring 151.

A person of ordinary skill in the art would understand that different components of an endoscopic camera, such as a camera sleeve, can be manufactured using the same preferred polymeric material that is disclosed herein.

The foregoing detailed description is provided to describe the invention in detail, and is not intended to limit the invention. In particular, the present invention may be used in the manufacture of medical device components with similar sizes, geometry and functions as the knob sub-assemblies described herein. Those skilled in the art will appreciate that various modifications may be made to the invention without departing significantly from the spirit and scope thereof.

What is claimed is:

1. A method of manufacturing a knob assembly, the method comprising:
   forming a first plastic blank using a plastic injection molding process, the first plastic blank having a shell, an interior surface, an exterior surface, a first end, a second end, a sprue, a center web, at least one rib extending from the interior surface, a floor adjoining the interior surface at the second end, at least one boss extending from the floor, and a groove on the interior surface at the first end;
   forming a second plastic blank using a plastic injection molding process, the second plastic blank having a sprue, a center web, and a skirt, the center web of the second plastic blank having at least one recess;
   trimming the sprues of the first plastic blank and the second plastic blank;
   machining an o-ring pocket into the first plastic blank;
   inserting a ring into the first plastic blank, the ring having an inside diameter and at least one groove on the inside diameter, the ring positioned on the floor and aligned between the at least one rib and the at least one boss;
   welding the skirt of the second plastic blank to the groove of the first plastic blank to form the knob assembly, the knob assembly covering at least a portion of the ring;
   machining an o-ring pocket and a stop groove into the second plastic blank of the knob assembly; and
   machining the exterior surface of the knob assembly.

2. The method of claim 1 further comprising laser marking the knob assembly.

3. The method of claim 2, wherein the laser marking step is performed with a green laser process.

4. The method of claim 1 wherein the center web of the first plastic blank is trimmed during the step of machining the o-ring pocket into the first plastic blank; and wherein the center web of the second plastic blank is trimmed during the step of machining the o-ring pocket and the stop groove into the second plastic blank of the knob assembly.

5. The method of claim 1 further comprising, after the step of inserting the ring into the first plastic blank, inserting at least one magnetic element into the at least one groove of the ring.

6. The method of claim 1 wherein the step of welding the skirt of the second plastic blank to the groove of the first plastic blank to form the knob assembly is performed using a spin-welding process.

7. The method of claim 6 wherein the groove of the first plastic blank comprises
a portion having approximately a forty-five degree slope;
the skirt of the second plastic blank comprises a tongue; and
the spin-welding process generates approximately a forty-five degree shear welded joint between the first plastic blank and the second plastic blank.

8. The method of claim 7 wherein the shear welded joint comprises a shutoff path having at least one gap defined between the first plastic blank and the second plastic blank.

9. The method of claim 1 wherein the first and second plastic blanks each consist essentially of from 0.1% to less than 1% mica, from 0.01% to 0.1% titanium dioxide, up to 0.01% tin oxide, from 0.02% to 0.2% colored metallic additives, and at least 99% polyphenylsulfone resin.

10. The method of claim 9 wherein the colored metallic additives comprise from 0.01% to 0.1% solvent blue 104 and from 0.01% to 0.1% solvent violet 13.

11. A method of manufacturing a camera having at least one knob assembly, the method comprising:
forming a first plastic blank using a plastic injection molding process, the first plastic blank having a shell, an interior surface, an exterior surface, a first end, a second end, a sprue, a center web, at least one rib extending from the interior surface, a floor adjoining the interior surface at the second end, at least one boss extending from the floor, and a groove on the interior surface at the first end;
forming a second plastic blank using a plastic injection molding process, the second plastic blank having a sprue, a center web, and a skirt, the center web of the second plastic blank having at least one recess;
trimming the sprues of the first plastic blank and the second plastic blank;
machining an o-ring pocket into the first plastic blank;
inserting a ring into the first plastic blank, the ring having an inside diameter and at least one groove on the inside diameter, the ring positioned on the floor and aligned between the at least one rib and the at least one boss;
welding the skirt of the second plastic blank to the groove of the first plastic blank to form the knob assembly, the knob assembly covering at least a portion of the ring;
machining an o-ring pocket and a stop groove into the second plastic blank of the knob assembly;
machining the exterior surface of the knob assembly; and
assembling the knob assembly into the camera.

12. A method of manufacturing a knob assembly, the method comprising:
forming a first metal blank using a metal injection molding process, the first metal blank comprising a ring having a first end, a second end, an outside diameter, an inside diameter, at least one groove on the inside diameter, a stop groove on the first end, and at least one boss extending from the outside diameter;
forming a second metal blank using a metal injection process, the second metal blank comprising a ring having an outside diameter, an inside diameter, and a skirt extending from the inside diameter of the second metal blank;
assembling the first and second metal blanks to form an inner ring;
over-molding the inner ring with a plastic material using a plastic injection molding system to form a knob assembly; and
post-machining the knob assembly.

13. The method of claim 12 wherein the step of post-machining the knob assembly comprises trimming portions of the plastic material of the knob assembly.

14. The method of claim 12 wherein the step of assembling the first and second metal blanks to form the inner ring is performed by one of a co-sintering process, a mechanical fit process, and a bonding process.

15. The method of claim 12 wherein the plastic material consists essentially of from 0.1% to less than 1% mica, from 0.01 to 0.1% titanium dioxide, up to 0.01% tin oxide, from 0.02 to 0.2% colored metallic additives, and at least 99% polyphenylsulfone resin.

16. The method of claim 15 wherein the colored metallic additives comprise from 0.01% to 0.1% solvent blue 104 and from 0.01% to 0.1% solvent violet 13.

17. The method of claim 12 further comprising laser marking the knob assembly.

18. The method of claim 17 wherein the laser marking step is performed with a green laser process.

19. The method of claim 12 further including, after post-machining the knob assembly, inserting at least one magnetic element into the at least one groove of the inner ring.

20. A method of manufacturing a camera having at least one knob assembly, the method comprising:
forming a first metal blank using a metal injection molding process, the first metal blank comprising a ring having a first end, a second end, an outside diameter, an inside diameter, at least one groove on the inside diameter, a stop groove on the first end, and at least one boss extending from the outside diameter;
forming a second metal blank using a metal injection process, the second metal blank comprising a ring having an outside diameter, an inside diameter, and a skirt extending from the inside diameter of the second metal blank;
assembling the first and second metal blanks to form an inner ring;
over-molding the inner ring with a plastic material using a plastic injection molding system to form the at least one knob assembly;
post-machining the knob assembly;
laser marking the knob assembly; and
assembling the knob assembly into the camera.

* * * * *